(12) United States Patent
Zhang et al.

(10) Patent No.: US 10,105,071 B2
(45) Date of Patent: Oct. 23, 2018

(54) METHOD AND DEVICE FOR ACQUIRING ECG DATA AND ECG DETECTION SYSTEM

(71) Applicants: BOE TECHNOLOGY GROUP CO., LTD., Beijing (CN); BEIJING BOE OPTOELECTRONICS TECHNOLOGY CO., LTD., Beijing (CN)

(72) Inventors: Yong Zhang, Beijing (CN); Shijun Wang, Beijing (CN); Yanna Xue, Beijing (CN); Wenbo Jiang, Beijing (CN); Yue Li, Beijing (CN); Zhiying Bao, Beijing (CN); Wenjun Xiao, Beijing (CN); Xiaoqing Peng, Beijing (CN); Zhenhua Lv, Beijing (CN)

(73) Assignees: BOE TECHNOLOGY GROUP CO., LTD., Beijing (CN); BEIJING BOE OPTOELECTRONICS TECHNOLOGY CO., LTD., Beijing (CN)

( * ) Notice: Subject to any disclaimer, the term of this patent is extended or adjusted under 35 U.S.C. 154(b) by 9 days.

(21) Appl. No.: 15/098,782

(22) Filed: Apr. 14, 2016

(65) Prior Publication Data

US 2017/0079540 A1 Mar. 23, 2017

(30) Foreign Application Priority Data

Sep. 23, 2015 (CN) .......................... 2015 1 0612765

(51) Int. Cl.
*A61B 5/04* (2006.01)
*A61B 5/00* (2006.01)
*A61B 5/0408* (2006.01)

(52) U.S. Cl.
CPC .......... *A61B 5/04017* (2013.01); *A61B 5/002* (2013.01); *A61B 5/0006* (2013.01); *A61B 5/0408* (2013.01)

(58) Field of Classification Search
CPC ... A61B 5/04017; A61B 5/0006; A61B 5/002; A61B 5/0408
(Continued)

(56) References Cited

U.S. PATENT DOCUMENTS

2013/0204100 A1  8/2013  Acquista
2013/0345540 A1  12/2013  Salazar et al.

FOREIGN PATENT DOCUMENTS

CN  201200400 Y  3/2009
CN  102688033 A  9/2012
(Continued)

OTHER PUBLICATIONS

First Chinese Office Action dated Aug. 3, 2017.

*Primary Examiner* — Amanda Hulbert
(74) *Attorney, Agent, or Firm* — Dilworth & Barrese, LLP.; Michael J. Musella, Esq.

(57) ABSTRACT

Embodiments of the present application provide a method and a device for acquiring ECG data, and an ECG detection system. A method for acquiring ECG data, comprising: acquiring ECG signals of heart; performing a first-stage amplification on the ECG signals, a multiple of the first-stage amplification including 5 to 10 times; performing band-pass filtering process within a first frequency range on the ECG signals on which the first-stage amplification has been performed, the first frequency range being 0.1 Hz to 50 Hz; performing a second-stage amplification on the ECG signals on which the band-pass filtering process has been performed, a multiple of the second-stage amplification including 40 to 50 times; performing analog-to-digital conversion on the ECG signals on which the second-stage
(Continued)

amplification has been performed, to generate ECG digital signals; and outputting the ECG digital signals.

20 Claims, 6 Drawing Sheets

(58) Field of Classification Search
USPC .............................................. 600/509; 607/17
See application file for complete search history.

(56) References Cited

FOREIGN PATENT DOCUMENTS

| | | |
|---|---|---|
| CN | 102908137 A | 2/2013 |
| CN | 103393418 A | 11/2013 |
| CN | 204121010 U | 1/2015 |
| CN | 104434085 A | 3/2015 |
| CN | 204542121 U | 8/2015 |
| JP | H0956686 A | 3/1997 |

US 10,105,071 B2

METHOD AND DEVICE FOR ACQUIRING ECG DATA AND ECG DETECTION SYSTEM

TECHNICAL FIELD

Embodiments of the present application relate to the field of ECG detection, and more particularly, to a method and a device for acquiring ECG data, and an ECG detection system.

BACKGROUND

To more conveniently detect body health, a mobile ECG detection system is being applied to medical treatment, in which mobile phones can be used to detect ECG, which is simple and easy to operate.

For example, as shown in FIG. 1, a mobile ECG detection system 10 in the prior art comprises a mobile display device 11, a sensing electrode 12, and an ECG detection device 13. The ECG detection device 13 is typically set as square, with the sensing electrode 12 being provided on each of its three side walls. In general, among the three sensing electrodes, two are right-hand sensing electrodes 121, one is a left-hand sensing electrode 122. At the time of using, palm and fingers of the right hand contact with the two right-hand sensing electrodes 121, respectively, and the left hand contacts with the left-hand sensing electrode 122. The sensing electrode 12 is for acquiring ECG signals of heart and transmitting the ECG signals to the ECG detection device 13, the ECG detection device 13 amplifies the received ECG signals and converts them into ECG digital signals. The mobile display device 11 (such as a mobile phone) may be connected with the ECG detection device 13 and make a display after acquiring the ECG digital signals.

However, the inventor has found that, since mobile ECG detection is carried out in daily life, it is seriously interfered by daily environment, the detected ECG data is inaccurate, which will affect an accurate judgment for disease.

SUMMARY

The embodiments of the present application provide a method and a device for acquiring ECG data, and an ECG detection system, the method for acquiring ECG data performs processing such as filtering on the acquired ECG signals, to improve accuracy of ECG data.

To achieve the above object, the embodiments of the present application adopt the following technical solutions:

An embodiment of the present application provides a method for acquiring ECG data, comprising:

acquiring ECG signals of heart;

performing a first-stage amplification on the ECG signals, a multiple of the first-stage amplification including 5 to 10 times;

performing band-pass filtering process within a first frequency range on the ECG signals on which the first-stage amplification has been performed, the first frequency range being 0.1 Hz to 50 Hz;

performing a second-stage amplification on the ECG signals on which the band-pass filtering process has been performed, a multiple of the second-stage amplification including 40 to 50 times;

performing analog-to-digital conversion on the ECG signals on which the second-stage amplification has been performed, to generate ECG digital signals; and outputting the ECG digital signals.

Alternatively, after performing band-pass filtering process within a first frequency range on the ECG signals on which the first-stage amplification has been performed, and prior to performing a second-stage amplification on the ECG signals on which the band-pass filtering process has been performed, the method further comprises:

performing signal attenuation whose attenuation range is −35 dB to −45 dB on an ECG signal corresponding to 50 Hz among the ECG signals on which the band-pass filtering process has been performed.

Alternatively, signal attenuation of −39.6 dB is performed on the ECG signal corresponding to 50 Hz among the ECG signals on which the band-pass filtering process has been performed.

Alternatively, after performing analog-to-digital conversion on the ECG signals on which the second-stage amplification has been performed, and prior to outputting the ECG digital signals, the method further comprises:

performing signal attenuation on an ECG digital signal corresponding to an ECG signal of 50 Hz among the ECG digital signals, the signal attenuation being used to counteract interference generated by the analog-to-digital conversion.

Alternatively, performing analog-to-digital conversion on the ECG signals on which the second-stage amplification has been performed comprises: adopting a sampling frequency of 50 Hz to perform analog-to-digital conversion on the ECG signals on which the second-stage amplification has been performed;

performing signal attenuation on an ECG digital signal corresponding to an ECG signal of 50 Hz among the ECG digital signals comprises: performing signal attenuation whose attenuation range is −55 dB to −65 dB on an ECG digital signal corresponding to an ECG signal of 50 Hz among the ECG digital signals received.

Alternatively, performing signal attenuation on an ECG digital signal corresponding to an ECG signal of 50 Hz among the ECG digital signals comprises: performing signal attenuation of −59.6 dB on the ECG digital signal corresponding to the ECG signal of 50 Hz among the ECG digital signals received.

An embodiment of the present application provides a device for acquiring ECG data, comprising: an electrode, a first-stage amplification unit, a first filtering unit, a second-stage amplification unit, a signal conversion unit, and a transmission unit, wherein the electrode is for being placed on a human body to acquire ECG signals of heart and transmit the ECG signals to the first-stage amplification unit;

the first-stage amplification unit is connected to the electrode, and for receiving the ECG signals transmitted from the electrode, performing a first-stage amplification on the received ECG signals transmitted from the electrode, and transmitting them to the first filtering unit, a multiple of the first-stage amplification including 5 to 10 times;

the first filtering unit is connected to the first-stage amplification unit, and for receiving the ECG signals on which the first-stage amplification has been performed and transmitted from the first-stage amplification unit, performing band-pass filtering process within a first frequency range on the received ECG signals on which the first-stage amplification has been performed, and transmitting them to the second-stage amplification unit, the first frequency range being 0.1 Hz to 50 Hz;

the second-stage amplification unit is connected to the first filtering unit, and for receiving the ECG signals on which the band-pass filtering process has been performed and transmitted from the first filtering unit, performing a second-stage amplification on the received ECG signals on which the band-pass filtering process has been performed, and transmitting them to the signal conversion unit, a multiple of the second-stage amplification including 40 to 50 times;

the signal conversion unit is connected to the second-stage amplification unit, and for receiving the ECG signals on which the second-stage amplification has been performed, performing analog-to-digital conversion on the received ECG signals on which the second-stage amplification has been performed, to generate ECG digital signals and transmit them to the transmission unit; and the transmission unit is connected to the signal conversion unit, and for receiving and outputting the ECG digital signals.

Alternatively, the device for acquiring ECG data further comprises: an 50 Hz notch filtering unit via which the signal conversion unit is connected to the second-stage amplification unit, and for receiving the ECG signals on which the filtering process has been performed and transmitted from the first filtering unit, and performing signal attenuation whose attenuation range is −35 dB to −45 dB on an ECG signal corresponding to 50 Hz among the received ECG signals on which the band-pass filtering process has been performed, and transmitting it to the second-stage amplification unit.

Alternatively, the 50 Hz notch filtering unit is for: performing signal attenuation of −39.6 dB on the ECG signal corresponding to 50 Hz among the received ECG signals on which the band-pass filtering process has been performed.

Alternatively, the device for acquiring ECG data further comprises: a second filtering unit via which the transmission unit is connected to the signal conversion unit, and for receiving the ECG digital signals transmitted from the signal conversion unit, performing signal attenuation on an ECG digital signal corresponding to an ECG signal of 50 Hz among the received ECG digital signals transmitted from the signal conversion unit, and transmitting it to the transmission unit, the signal attenuation being used to counteract interference generated by the analog-to-digital conversion.

Alternatively, a sampling frequency of the signal conversion unit is 50 Hz;

the second filtering unit is for: performing signal attenuation whose attenuation range is −55 dB to −65 dB on an ECG digital signal corresponding to an ECG signal of 50 Hz among the received ECG digital signals transmitted from the signal conversion unit.

Alternatively, the second filtering unit is for: performing signal attenuation of −59.6 dB on an ECG digital signal corresponding to an ECG signal of 50 Hz among the received ECG digital signals transmitted from the signal conversion unit.

Alternatively, the transmission unit is a wireless transmission unit.

An embodiment of the present application provides an ECG detection system, comprising a display and any of the device for acquiring ECG data provided by an embodiment of the present application, the display being connected with the device for acquiring ECG data, and for receiving and displaying the ECG digital signals outputted by the device for acquiring ECG data.

The embodiments of the present application provide a method and a device for acquiring ECG data, and an ECG detection system, ECG signals are acquired through an electrode, before the ECG signals are transmitted to an A/D converter for digital-to-analog conversion, a first-stage amplification of 5 to 10 multiples is performed on the ECG signals, to avoid a too high magnification multiple and a serious interference from affecting accuracy of the ECG signals; thereafter, since main energy of the ECG signals is concentrated in a range of 0.1 Hz to 50 Hz, thus in the method of acquiring the ECG data in the embodiments of the present application, higher and lower limiting frequencies are designed as 50 Hz and 0.1 Hz, respectively, only the ECG signals in the frequency range of 0.1 Hz to 50 Hz below are acquired and detected, so the ECG signals acquired are closer to actual ECG signals of a human body, detection is more accurate; a second-stage amplification is performed on the ECG signals on which the band-pass filtering process has been performed, to amplify them to ECG analog signals required for performing digital-to-analog conversion by the A/D converter.

BRIEF DESCRIPTION OF THE DRAWINGS

In order to more clearly explain the technical solutions in the embodiments of the present application or in the prior art, drawings necessary for descriptions of the embodiments of the present application or the prior art will be introduced briefly, obviously, the drawings described below are merely some embodiments of the present application, for those of ordinary skill in the art, it is possible to attain other drawings based on these drawings without paying creative effort.

REFERENCE SIGNS

11—Mobile display device; 12—Sensing electrode; 13—ECG detection device; 121—Right-hand sensing electrode; 122—Left-hand sensing electrode.

DETAILED DESCRIPTION OF THE EMBODIMENTS

Hereinafter, the technical solutions in the embodiments of the present application will be described clearly and comprehensively in combination with the drawings in the embodiments of the present application, obviously, these described embodiments are parts of the embodiments of the present application, rather than all of the embodiments thereof. All the other embodiments obtained by those skilled in the art based on the embodiments of the present application without paying creative efforts fall into the protection scope of the present application.

Figure 1:
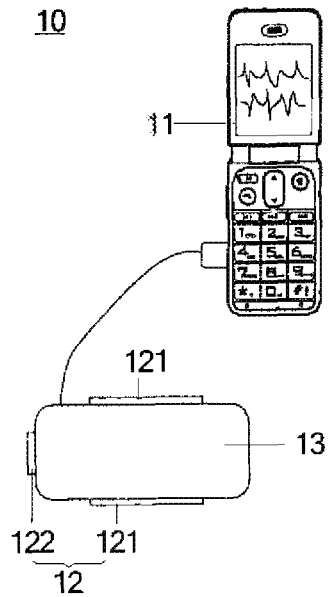
FIG. 1 is a schematic diagram of a mobile ECG detection system in the prior art.
Figure 2:
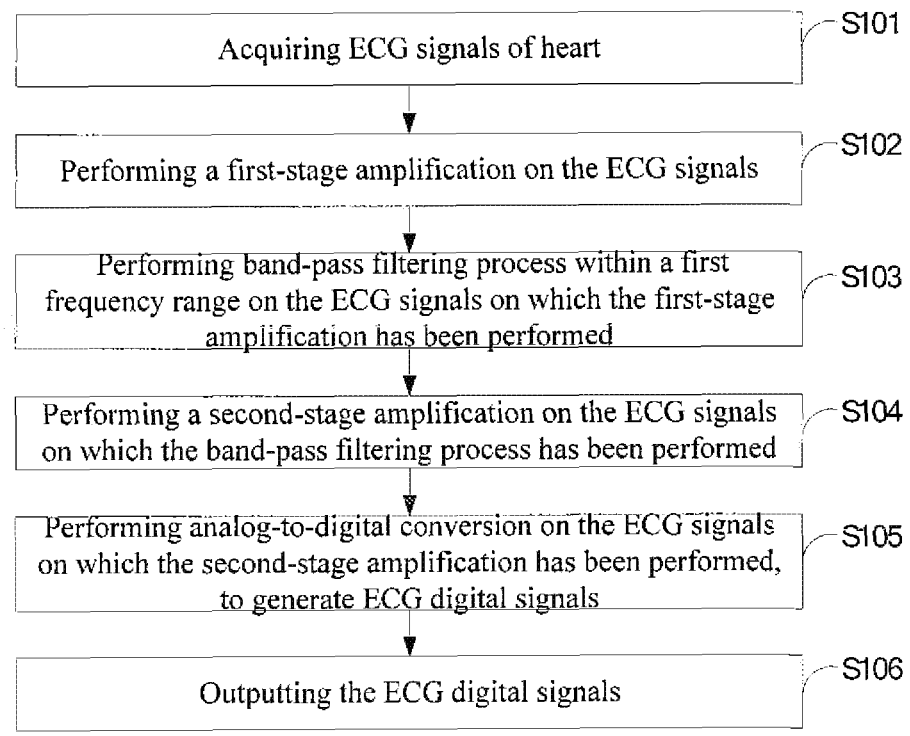
FIG. 2 is a schematic diagram of a method for acquiring ECG data provided by an embodiment of the present application.

An embodiment of the present application provides a method for acquiring ECG data, as shown in FIG. 2, comprising:

Step 101, acquiring ECG signals of heart. Acquiring ECG signals may be implemented through an electrode in particular, wherein for the sake of accuracy of acquiring ECG signals, ECG signals of heart are usually acquired through two right-hand electrodes and one left-hand electrode.

Step 102, performing a first-stage amplification on the ECG signals, a multiple of the first-stage amplification including 5 to 10 times. It needs to be noted that, the ECG signals acquired through the electrode usually need to pass through an A/D converter and be converted into digital signals to display. Before the ECG signals are transmitted to the A/D converter for analog-to-digital conversion, the ECG signals need to be amplified, that is, they are amplified to ECG analog signals required for performing analog-to-digital conversion by the A/D converter. However, since the electrode acquires the ECG signals in daily life where a lot of environmental interference exists, the interference will be amplified when amplifying the ECG signals, thus, in the method for acquiring ECG signals provided by the embodiment of the present application, first, a first-stage amplification of 5 to 10 multiples is performed on the ECG signals, to avoid a too high magnification multiple and a serious interference from affecting accuracy of the ECG signals.

Step 103, performing band-pass filtering process within a first frequency range on the ECG signals on which the first-stage amplification has been performed, the first frequency range being 0.1 Hz to 50 Hz.

It needs to be noted that the range of value in the embodiment of the present application all includes end values, for example, the first frequency range is 0.1 Hz to 50 Hz, i.e., the first frequency range includes 0.1 Hz and 50 Hz. ECG Signal detection belongs to detecting ultra-low frequency weak signals whose amplitude is at an order of mV and frequency range is about 0.05 Hz-100 Hz in a background with strong noise. Since main energy of the ECG signals is concentrated in a range of 0.1 Hz to 50 Hz, thus in the method of acquiring the ECG data in the embodiment of the present application, higher and lower limiting frequencies are designed as 50 Hz and 0.1 Hz, respectively, only the ECG signals in the frequency range of 0.1 Hz to 50 Hz below are acquired and detected, so the ECG signals acquired are closer to actual ECG signals of a human body, detection is more accurate.

Step 104, performing a second-stage amplification on the ECG signals on which the band-pass filtering process has been performed, a multiple of the second-stage amplification including 40 to 50 times. That is, the second-stage amplification is performed on the ECG signals, they are amplified to ECG analog signals required for performing digital-to-analog conversion by the A/D converter.

Step 105, performing analog-to-digital conversion on the ECG signals on which the second-stage amplification has been performed, to generate ECG digital signals. The analog-to-digital conversion may be performed on the ECG signals on which the second-stage amplification has been performed by an A/D converter in particular.

Step 106, outputting the ECG digital signals.

The embodiment of the present application provides a method for acquiring ECG data, ECG signals are acquired through an electrode, before the ECG signals are transmitted to an A/D converter for digital-to-analog conversion, a first-stage amplification of 5 to 10 multiples is performed on the ECG signals, to avoid too high magnification multiple and serious interference from affecting accuracy of the ECG signals; thereafter, since main energy of the ECG signals is concentrated in a range of 0.1 Hz to 50 Hz, thus in the method of acquiring the ECG data in the embodiment of the present application, higher and lower limiting frequencies are designed as 50 Hz and 0.1 Hz, respectively, only the ECG signals in the frequency range of 0.1 Hz to 50 Hz below are acquired and detected, so the ECG signals acquired are closer to actual ECG signals of a human body, detection is more accurate; a second-stage amplification is performed on the ECG signals on which the band-pass filtering process has been performed, to amplify them to ECG analog signals required for performing digital-to-analog conversion by the A/D converter.

Figure 3:
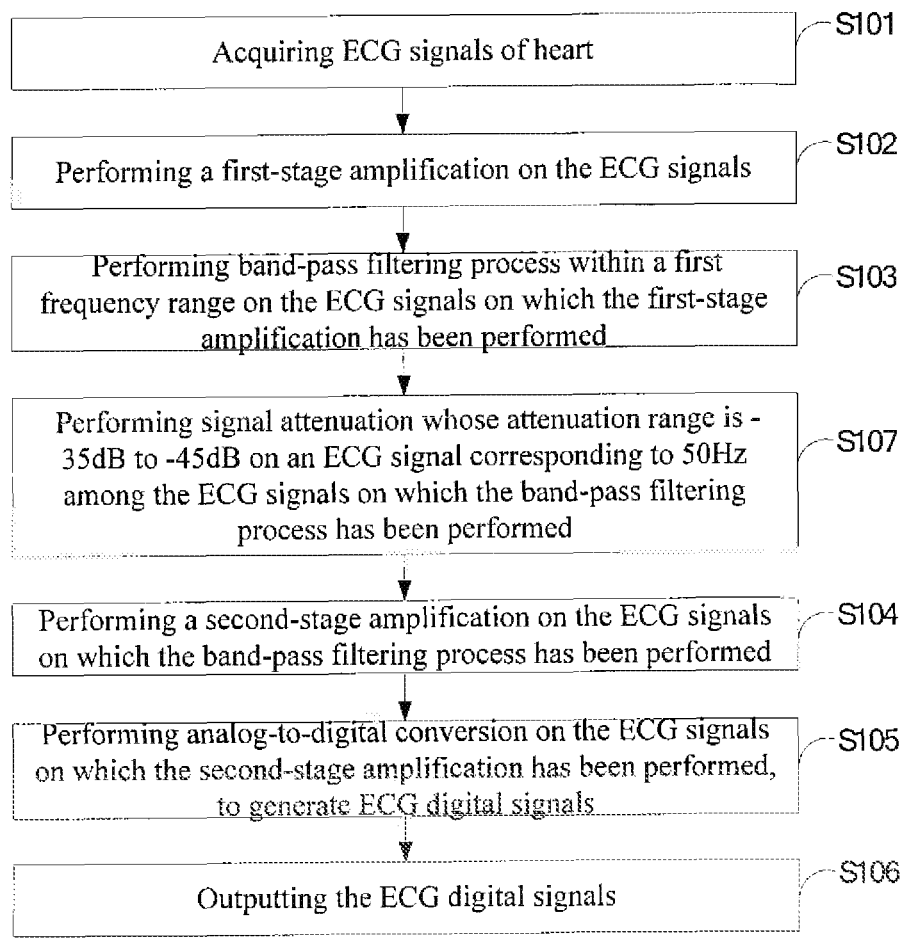
FIG. 3 is another schematic diagram of a method for acquiring ECG data provided by an embodiment of the present application.

Alternatively, as shown in FIG. 3, after step 103 and before step 104, the method further comprises:

Step 107, performing signal attenuation whose attenuation range is −35 dB to −45 dB on an ECG signal corresponding to 50 Hz among the ECG signals on which the band-pass filtering process has been performed. Since in a daily life environment, there is 50 Hz-frequency power-line interference, in the method for acquiring ECG signals provided by the embodiment of the present application, signal attenuation whose attenuation range is −35 dB to −45 dB is performed on an ECG signal of 50 Hz, to improve accuracy of the ECG signals. And after multiple tests and studies, the inventor has found that the ECG signals attenuated by −39.6 dB has the highest accuracy.

Figure 4:
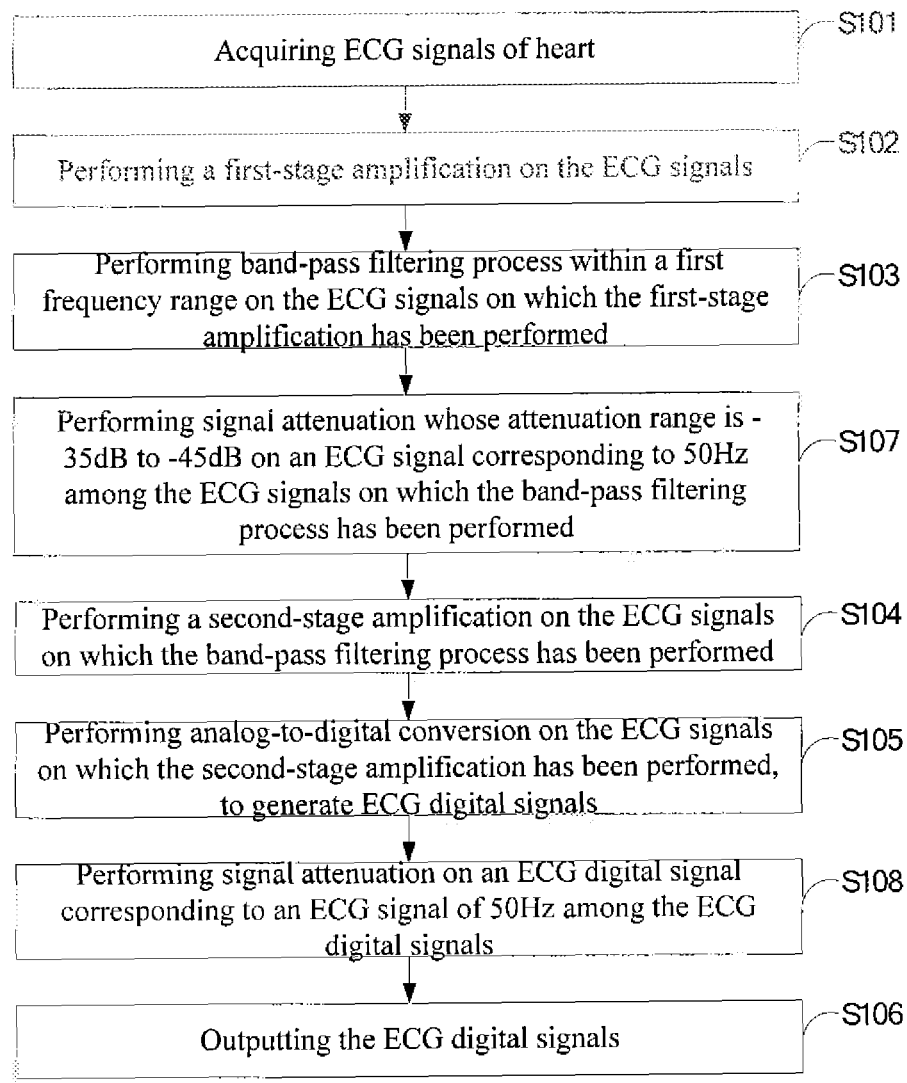
FIG. 4 is another schematic diagram of a method for acquiring ECG data provided by an embodiment of the present application.
Figure 5:
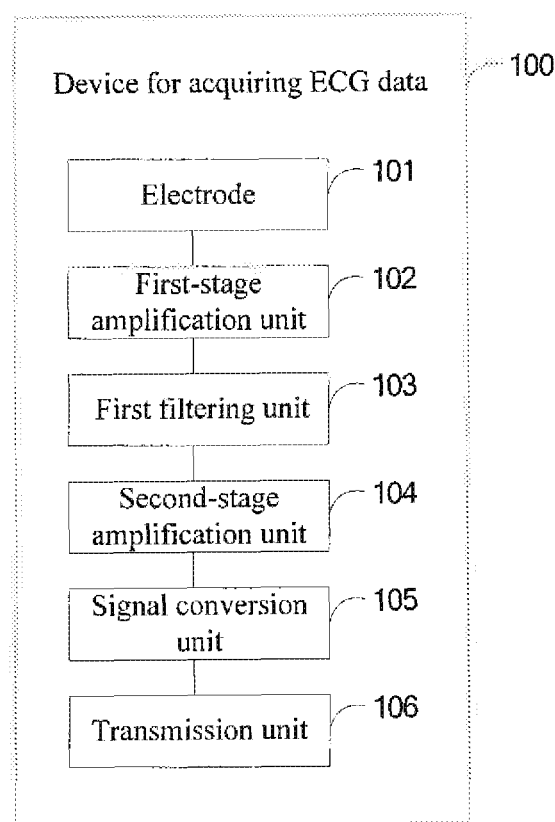
FIG. 5 is a schematic diagram of a device for acquiring ECG data provided by an embodiment of the present application.

Alternatively, as shown in FIG. 4, after step 105 and before step 106, the method further comprises:

Step 108, performing signal attenuation on an ECG digital signal corresponding to an ECG signal of 50 Hz among the ECG digital signals, the signal attenuation being used to counteract interference generated by the analog-to-digital conversion. Because when performing digital-to-analog conversion on the ECG signals, it may generate interference signals that are mainly concentrated at 50 Hz, thus step 108 in the embodiment of the present application performs signal attenuation on an ECG digital signal corresponding to an ECG signal of 50 Hz, to counteract interference generated by the analog-to-digital conversion, which further improves accuracy.

Alternatively, step 105 comprises: adopting a sampling frequency of 50 Hz to perform analog-to-digital conversion on the ECG signals on which the second-stage amplification has been performed. Then, step 108 comprises: performing signal attenuation whose attenuation range is −55 dB to −65 dB on an ECG digital signal corresponding to an ECG signal of 50 Hz among the ECG digital signals received.

And after multiple tests and studies, the inventor has found that when adopting the sampling frequency of 50 Hz to perform analog-to-digital conversion on the ECG signals no which the second-stage amplification has been performed, performing signal attenuation whose attenuation range is −55 dB to −65 dB on an ECG digital signal corresponding to an ECG signal of 50 Hz among the ECG digital signals received can acquire ECG signals that are more actual and accurate. Alternatively, performing signal attenuation of −59.6 dB on an ECG digital signal corresponding to an ECG signal of 50 Hz can achieve the highest accuracy.

Next, an embodiment of the present application provides a device for acquiring ECG data corresponding to the method for acquiring ECG data in the embodiment of the present application, it needs to the noted that respective functional units included in the device can execute corresponding steps in the above method, so respective functional units of the device in the following embodiment will not be described in detail.

An embodiment of the present application provides a device 100 for acquiring ECG data, comprising: an electrode 101, a first-stage amplification unit 102, a first filtering unit 103, a second-stage amplification unit 104, a signal conversion unit 105, and a transmission unit 106.

The electrode 101 is for being placed on a human body to acquire ECG signals of heart and transmit the ECG signals to the first-stage amplification unit.

The first-stage amplification unit 102 is connected to the electrode, and for receiving the ECG signals transmitted from the electrode, performing a first-stage amplification on the received ECG signals transmitted from the electrode, and transmitting them to the first filtering unit, a multiple of the first-stage amplification including 5 to 10 times.

The first filtering unit 103 is connected to the first-stage amplification unit, and for receiving the ECG signals on which the first-stage amplification has been performed and transmitted from the first-stage amplification unit, performing band-pass filtering process within a first frequency range on the received ECG signals on which the first-stage amplification has been performed, and transmitting them to the second-stage amplification unit, the first frequency range being 0.1 Hz to 50 Hz.

The second-stage amplification unit 104 is connected to the first filtering unit, and for receiving the ECG signals on which the band-pass filtering process has been performed and transmitted from the first filtering unit, performing a second-stage amplification on the received ECG signals on which the band-pass filtering process has been performed, and transmitting them to the signal conversion unit, a multiple of the second-stage amplification including 40 to 50 times.

The signal conversion unit 105 is connected to the second-stage amplification unit, and for receiving the ECG signals on which the second-stage amplification has been performed, performing analog-to-digital conversion on the received ECG signals on which the second-stage amplification has been performed, to generate ECG digital signals and transmit them to the transmission unit. For example, the signal conversion unit may be an A/D converter.

The transmission unit 106 is connected to the signal conversion unit, and for receiving and outputting the ECG digital signals. Alternatively, the transmission unit is a wireless transmission unit. The wireless transmission unit may transmit the ECG digital signals through wireless protocols, which may for example be Bluetooth transmission. Bluetooth is a radio technique that supports short-range communications between devices (usually within 10 m), with which wireless information can be exchanged between many devices including mobile phones, tablet PCs, wireless headsets, laptop computers, related peripherals and so on. Bluetooth adopts a decentralized network structure and fast frequency hopping and short packetizing techniques, it supports point-to-point and point-to-multipoint communications, operates at a global general frequency band of 2.4 GHz ISM, i.e. industrial, scientific, and medical frequency bands. Its data rate is 1 Mbps. For example, any Bluetooth-enabled mobile phone can receive ECG digital signals, and further, receive and read ECG digital signals through software on the mobile phone and display the ECG.

The embodiment of the present application provides a device for acquiring ECG data, before the ECG signals are transmitted to the signal conversion unit for digital-to-analog conversion, a first-stage amplification of 5 to 10 multiples is performed on the ECG signals, to avoid too high magnification multiple and serious interference from affecting accuracy of the ECG signals; thereafter, since main energy of the ECG signals is concentrated in a range of 0.1 Hz to 50 Hz, thus the limiting frequencies of the first filtering unit in the embodiment of the present application are designed as 50 Hz and 0.1 Hz, respectively, only the ECG signals in the frequency range of 0.1 Hz to 50 Hz are acquired and detected, to avoid signal interference in other frequencies; a second-stage amplification is performed on the ECG signals on which the band-pass filtering process has been performed, to amplify them to ECG analog signals required for performing digital-to-analog conversion by the signal conversion unit.

Figure 6:
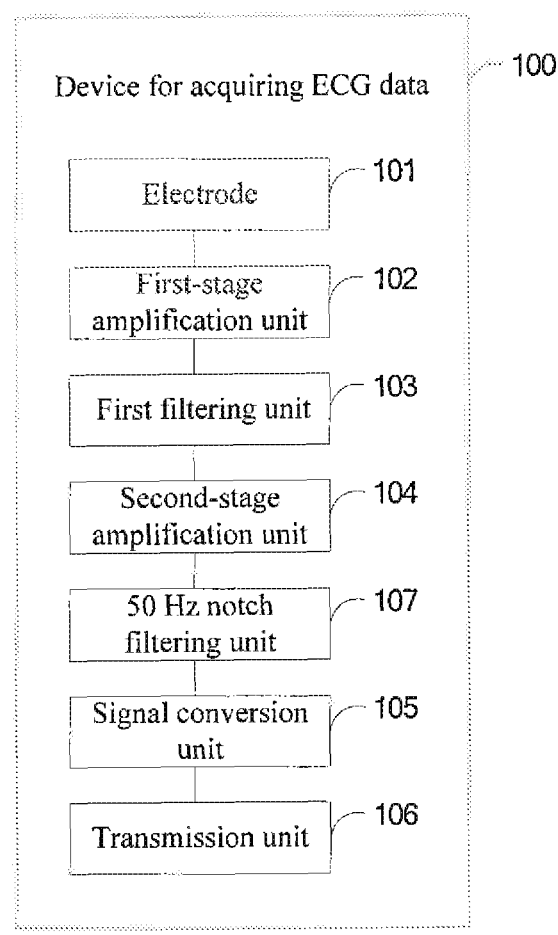
FIG. 6 is another schematic diagram of a device for acquiring ECG data provided by an embodiment of the present application.

Alternatively, as shown in FIG. 6, the device 100 for acquiring ECG data further comprises: an 50 Hz notch filtering unit 107 via which the signal conversion unit 105 is connected to the second-stage amplification unit 104, and for receiving the ECG signals on which the filtering process has been performed and transmitted from the first filtering unit 103 and performing signal attenuation whose attenuation range is −35 dB to −45 dB on an ECG signal corresponding to 50 Hz among the received ECG signals on which the band-pass filtering process has been performed, and transmitting it to the second-stage amplification unit 104.

Alternatively, the 50 Hz notch filtering unit 107 is for: performing signal attenuation of −39.6 dB on an ECG signal corresponding to 50 Hz among the received ECG signals on which the band-pass filtering process has been performed.

Figure 7:
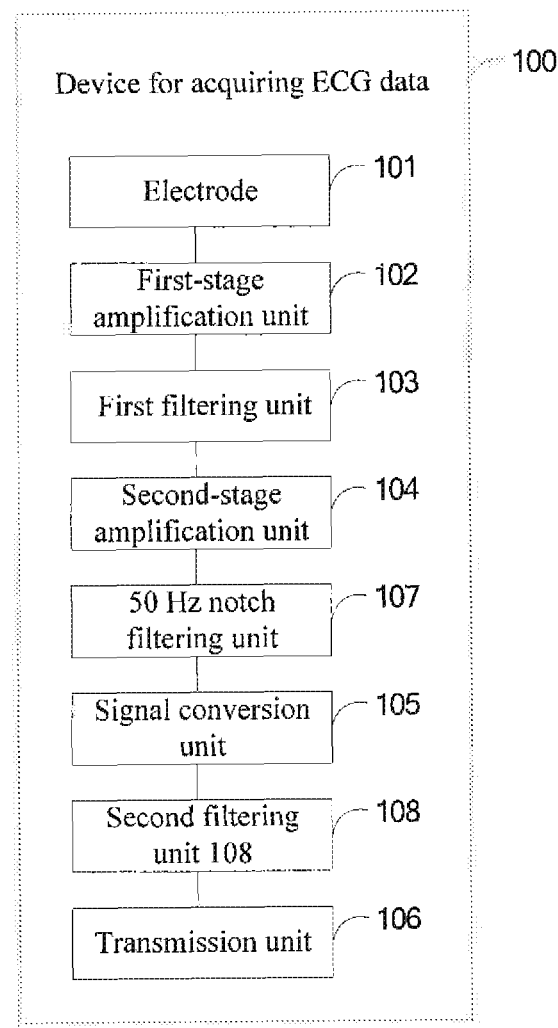
FIG. 7 is another schematic diagram of a device for acquiring ECG data provided by an embodiment of the present application.

Alternatively, as shown in FIG. 7, the device 100 for acquiring ECG data further comprises: a second filtering unit 108 via which the transmission unit 106 is connected to the signal conversion unit 105, and for receiving the ECG digital signals transmitted from the signal conversion unit 105, performing signal attenuation on an ECG digital signal corresponding to an ECG signal of 50 Hz among the received ECG digital signals transmitted from the signal conversion unit 105, and transmitting it to the transmission unit 106, the signal attenuation being used to counteract interference generated by the analog-to-digital conversion.

Alternatively, a sampling frequency of the signal conversion unit is 50 Hz; the second filtering unit 108 is for: performing signal attenuation whose attenuation range is −55 dB to −65 dB on an ECG digital signal corresponding to an ECG signal of 50 Hz among the received ECG digital signals transmitted from the signal conversion unit 105. Further, the second filtering unit 108 is for: performing signal attenuation of −59.6 dB on an ECG digital signal corresponding to an ECG signal of 50 Hz among the received ECG digital signals transmitted from the signal conversion unit.

It should be noted that in the embodiment of the present application, respective units in the device for acquiring ECG data, including the electrode, the first-stage amplification unit, the first filtering unit, the second-stage amplification unit, the signal conversion unit, the transmission unit, and 50 Hz notch filtering unit, and so on all have a standard operating voltage of 3.3V, so power supply of the entire system adopts 3.3V. Therefore, it is possible to adopt a portable battery to provide an electrical signal to the device for acquiring ECG data, which facilitates using portability of the device for acquiring ECG data.

An embodiment of the present application provides an ECG detection system, comprising a display and any of the device for acquiring ECG data provided by an embodiment of the present application, the display being connected with the device for acquiring ECG data, and for receiving and displaying the ECG digital signals outputted by the device for acquiring ECG data.

For example, the display may be a mobile phone, on which software may be run to receive ECG digital signals and render an ECG waveform in real-time according to the received ECG digital signal. Furthermore, the display may further include a storage unit, which stores in real time the received ECG digital signals, transmit the ECG digital signals via a storage medium or a wireless network to large computing storage devices such as computers if condition permits, to better analyze the ECG data.

As will be appreciated by those of ordinary skill in the art: all or part of the steps of the above method embodiments may be completed by instructing relevant hardware through programs, these programs may be stored in a computer readable storage medium, the steps included in the above method embodiments will be executed when the programs are executed; the aforesaid storage medium includes various mediums capable of storing program codes like a mobile storage device, a Read Only Memory (ROM), a magnetic disk, or an optical disk.

The above described are merely specific implementations of the present application, however, the protection scope of the present application is limited thereto, modifications or replacements that are easily conceivable for those skilled in the art within the technique range disclosed in the present application should all fall into the protection scope of the present application. Therefore, the protection scope of the present application should be based on what is claimed in the claims.

The application claims priority of Chinese Patent Application No. 201510612765.5 filed on Sep. 23, 2015, the disclosure of which is incorporated herein by reference in its entirety as part of the present application.

What is claimed is:

1. A method for acquiring ECG data, comprising:
acquiring ECG signals of heart;
performing a first-stage amplification on the ECG signals, a multiple of the first-stage amplification including 5 to 10 times;
performing band-pass filtering process within a first frequency range on the ECG signals on which the first-stage amplification has been performed, the first frequency range being 0.1 Hz to 50 Hz;
performing a second-stage amplification on the ECG signals on which the band-pass filtering process has been performed, a multiple of the second-stage amplification including 40 to 50 times;
performing analog-to-digital conversion on the ECG signals on which the second-stage amplification has been performed, to generate ECG digital signals; and
outputting the ECG digital signals.

2. The method for acquiring ECG data according to claim 1, wherein after performing band-pass filtering process within a first frequency range on the ECG signals on which the first-stage amplification has been performed, and prior to performing a second-stage amplification on the ECG signals on which the band-pass filtering process has been performed, the method further comprises:
performing signal attenuation whose attenuation range is −35 dB to −45 dB on an ECG signal corresponding to 50 Hz among the ECG signals on which the band-pass filtering process has been performed.

3. The method for acquiring ECG data according to claim 2, wherein signal attenuation of −39.6 dB is performed on the ECG signal corresponding to 50 Hz among the ECG signals on which the band-pass filtering process has been performed.

4. The method for acquiring ECG data according to claim 1, wherein after performing analog-to-digital conversion on the ECG signals on which the second-stage amplification has been performed, and prior to outputting the ECG digital signals, the method further comprises:
performing signal attenuation on an ECG digital signal corresponding to an ECG signal of 50 Hz among the ECG digital signals, the signal attenuation being used to counteract interference generated by the analog-to-digital conversion.

5. The method for acquiring ECG data according to claim 4, wherein performing analog-to-digital conversion on the ECG signals on which the second-stage amplification has been performed comprises: adopting a sampling frequency of 50 Hz to perform analog-to-digital conversion on the ECG signals on which the second-stage amplification has been performed;
performing signal attenuation on the ECG digital signal corresponding to the ECG signal of 50 Hz among the ECG digital signals comprises: performing signal attenuation whose attenuation range is −55 dB to −65 dB on the ECG digital signal corresponding to the ECG signal of 50 Hz among the ECG digital signals received.

6. The method for acquiring ECG data according to claim 5, wherein performing signal attenuation on the ECG digital signal corresponding to the ECG signal of 50 Hz among the ECG digital signals comprises: performing signal attenuation of −59.6 dB on the ECG digital signal corresponding to the ECG signal of 50 Hz among the ECG digital signals received.

7. A device for acquiring ECG data, comprising: an electrode, a first-stage amplification subcircuit, a first filtering subcircuit, a second-stage amplification subcircuit, an A/D converter, and a transmission subcircuit, wherein
the electrode is configured to be placed on a human body a configured to acquire ECG signals of heart and transmit the ECG signals to the first-stage amplification subcircuit;
the first-stage amplification subcircuit is configured to be connected to the electrode, and configured to receive the ECG signals transmitted from the electrode, perform a first-stage amplification on the received ECG signals transmitted from the electrode, and transmit them to the first filtering subcircuit, a multiple of the first-stage amplification being in a range of 5 to 10;
the first filtering subcircuit is configured to be connected to the first-stage amplification subcircuit and configured to receive the ECG signals on which the first-stage amplification has been performed and transmitted from the first-stage amplification subcircuit, perform band-pass filtering process within a first frequency range on the received ECG signals on which the first-stage amplification has been performed, and transmit them to the second-stage amplification subcircuit, the first frequency range being 0.1 Hz to 50 Hz;
the second-stage amplification subcircuit is configured to be connected to the first filtering subcircuit, and configured to receive the ECG signals on which the band-pass filtering process has been performed and transmitted from the first filtering subcircuit, perform a second-stage amplification on the received ECG signals on which the band-pass filtering process has been performed, and transmit them to the signal conversion subcircuit, a multiple of the second-stage amplification being in a range of 40 to 50;

the A/D converter is configured to be connected to the second-stage amplification subcircuit, and configured to receive the ECG signals on which the second-stage amplification has been performed, perform analog-to-digital conversion on the received ECG signals on which the second-stage amplification has been performed, to generate ECG digital signals and transmit them to the transmission subcircuit; and the transmission subcircuit is configured to be connected to the signal conversion subcircuit, and receive and output the ECG digital signals.

8. The device according to claim 7, further comprising: an 50 Hz notch filtering subcircuit via which the signal conversion subcircuit is connected to the second-stage amplification subcircuit, and configured to receive the ECG signals on which the filtering process has been performed and transmitted from the first filtering subcircuit, and perform signal attenuation whose attenuation range is −35 dB to −45 dB on an ECG signal corresponding to 50 Hz among the received ECG signals on which the band-pass filtering process has been performed, and transmit it to the second-stage amplification subcircuit.

9. The device according to claim 8, wherein the 50 Hz notch filtering subcircuit is further configured to perform signal attenuation of −39.6 dB on the ECG signal corresponding to 50 Hz among the received ECG signals on which the band-pass filtering process has been performed.

10. The device according to claim 7, further comprising: a second filtering subcircuit via which the transmission subcircuit is connected to the signal conversion subcircuit, and configured to be receive the ECG digital signals transmitted from the signal conversion subcircuit, perform signal attenuation on an ECG digital signal corresponding to an ECG signal of 50 Hz among the received ECG digital signals transmitted from the signal conversion subcircuit, and transmit it to the transmission subcircuit, the signal attenuation being used to counteract interference generated by the analog-to-digital conversion.

11. The device according to claim 10, wherein a sampling frequency of the signal conversion subcircuit is 50 Hz;

the second filtering subcircuit is configured to perform signal attenuation whose attenuation range is −55 dB to −65 dB on the ECG digital signal corresponding to the ECG signal of 50 Hz among the received ECG digital signals transmitted from the signal conversion subcircuit.

12. The device according to claim 11, wherein the second filtering subcircuit is configured to be perform signal attenuation of −59.6 dB on the ECG digital signal corresponding to the ECG signal of 50 Hz among the received ECG digital signals transmitted from the signal conversion subcircuit.

13. The device according to claim 7, wherein the transmission subcircuit is a wireless transmission subcircuit.

14. An ECG detection system, comprising a display and the device for acquiring ECG data according to claim 7, the display being connected with the device for acquiring ECG data, and for receiving and displaying the ECG digital signals outputted by the device for acquiring ECG data.

15. The ECG detection system according to claim 14, wherein the device for acquiring ECG data further comprises: an 50 Hz notch filtering subcircuit via which the signal conversion subcircuit is connected to the second-stage amplification subcircuit, and for receiving the ECG signals on which the filtering process has been performed and transmitted from the first filtering subcircuit, and performing signal attenuation whose attenuation range is −35 dB to −45 dB on an ECG signal corresponding to 50 Hz among the received ECG signals on which the band-pass filtering process has been performed, and transmitting it to the second-stage amplification subcircuit.

16. The ECG detection system according to claim 15, wherein the 50 Hz notch filtering subcircuit is for: performing signal attenuation of −39.6 dB on the ECG signal corresponding to 50 Hz among the received ECG signals on which the band-pass filtering process has been performed.

17. The ECG detection system according to claim 14, wherein the device for acquiring ECG data further comprises: a second filtering subcircuit via which the transmission subcircuit is connected to the signal conversion subcircuit, and for receiving the ECG digital signals transmitted from the signal conversion subcircuit, performing signal attenuation on an ECG digital signal corresponding to an ECG signal of 50 Hz among the received ECG digital signals transmitted from the signal conversion subcircuit, and transmitting it to the transmission subcircuit, the signal attenuation being used to counteract interference generated by the analog-to-digital conversion.

18. The ECG detection system according to claim 17, wherein a sampling frequency of the signal conversion subcircuit is 50 Hz;

the second filtering subcircuit is for: performing signal attenuation whose attenuation range is −55 dB to −65 dB on the ECG digital signal corresponding to the ECG signal of 50 Hz among the received ECG digital signals transmitted from the signal conversion subcircuit.

19. The ECG detection system according to claim 18, wherein the second filtering subcircuit is for: performing signal attenuation of −59.6 dB on the ECG digital signal corresponding to the ECG signal of 50 Hz among the received ECG digital signals transmitted from the signal conversion subcircuit.

20. The ECG detection system according to claim 19, wherein the transmission subcircuit is a wireless transmission subcircuit.

* * * * *